United States Patent [19]

Whitehead et al.

[11] Patent Number: 4,593,728
[45] Date of Patent: Jun. 10, 1986

[54] DISPENSING DEVICE AND RECORDING APPARATUS

[76] Inventors: Thomas P. Whitehead, 70 Northumberland Road, Leamington Spa, Warwickshire; Gary H. G. H. Thorpe, 84 Newcombe Road, Handsworth, Birmingham; Larry J. Kricka, 16 Newent Road, Northfield, Birmingham; John E. C. Gibbons, 9 Norfolk Close, Stirchley, Birmingham; Roger A. Bunce, 117 Berberry Close, Bournville, Birmingham, all of England

[21] Appl. No.: 626,856
[22] PCT Filed: Nov. 14, 1983
[86] PCT No.: PCT/GB83/00287
  § 371 Date: Jun. 27, 1984
  § 102(e) Date: Jun. 27, 1984
[87] PCT Pub. No.: WO84/02090
  PCT Pub. Date: Jun. 7, 1984

[30] Foreign Application Priority Data

Nov. 20, 1982 [GB] United Kingdom ............... 8233168
Apr. 26, 1983 [GB] United Kingdom ............... 8311372

[51] Int. Cl.[4] .............................................. B65B 3/04
[52] U.S. Cl. ................................... 141/98; 141/234; 73/864.01; 422/100
[58] Field of Search ..................... 141/37–67, 141/83, 250–284, 234–245, 98, 18–29; 73/864.01, 864.25; 422/100

[56] References Cited

U.S. PATENT DOCUMENTS

| | | | |
|---|---|---|---|
| 3,568,735 | 3/1971 | Lancaster | 73/425.6 |
| 3,627,431 | 12/1971 | Komarniski | 73/425.6 |
| 3,650,306 | 3/1972 | Lancaster | 141/238 |
| 3,696,971 | 10/1972 | Maclin | 73/425.6 |
| 3,923,462 | 12/1975 | Cavanagh | 73/425.6 |
| 3,982,438 | 9/1976 | Byrd | 73/425.6 |
| 4,027,979 | 6/1977 | Komarniski | 73/425.6 |
| 4,047,438 | 9/1977 | Sekine | 73/423 A |

FOREIGN PATENT DOCUMENTS

| | | |
|---|---|---|
| 563347 | 11/1943 | United Kingdom . |
| 729259 | 5/1955 | United Kingdom . |
| 1305815 | 2/1973 | United Kingdom . |
| 1363540 | 8/1974 | United Kingdom . |
| 1539910 | 2/1979 | United Kingdom . |

OTHER PUBLICATIONS

Industrial Laboratory, vol. 40, No. 8, Feb. 1975, p. 1118, lines 11–19.

*Primary Examiner*—Houston S. Bell, Jr.
*Attorney, Agent, or Firm*—Holman & Stern

[57] ABSTRACT

A dispensing device, for dispensing reagent into an array of reaction wells (16) in a photographic recording apparatus, comprises an array of tubes (28) which are mounted in a support (23). The support (23) contains a common chamber (29) into which the tops of all the tubes (28) open. The chamber (29) is connected with atmosphere via an opening (32) which is sealable manually to retain liquid in the tubes (28) when the latter are immersed in a reservoir (40) and which is unsealed to dispense the liquid. The recording apparatus has a housing (10) closable at the top by part of the support (23). A plate (11) having an array of holes (15) therethrough rests on a shutter (13) disposed above a photographic film holder (12). The plate (11) carries the reaction wells (16) in the holes (15).

32 Claims, 11 Drawing Figures

DISPENSING DEVICE AND RECORDING APPARATUS

CROSS REFERENCE TO RELATED APPLICATION(S)

This U.S. application stems from PCT International Application No. PCT/GB83/00287 filed Nov. 14, 1983.

BACKGROUND OF THE INVENTION

1. Field of the Invention

This invention relates to a dispensing device for simultaneously dispensing a multiplicity of predetermined quantities of liquid. Such dispensing devices are useful, for example, in testing where it is necessary to supply predetermined quantities of liquid reagent to separate vessels. This invention also relates to apparatus for recording a multiplicity of reactions effected simultaneously in separate vessels. The invention is particularly, though not exclusively, concerned with improving the efficiency of biochemical analyses where large numbers of biochemical tests are required to be conducted speedily and efficiently.

2. Description of the Prior Art

Various devices have been proposed for dispensing liquid into a number of vessels. For example, it has been proposed to dispense liquid by use of a row of pipettes each having a plunger associated therewith, the plungers being connected to a common operating device which may be operated mechanically or manually to draw liquid into the pipettes and subsequently to dispense it. Examples of such devices are disclosed in U.S. Pat. Nos. 3,568,735 to Lancaster (Class 141/238) and to Sekine (Class 73/423); 4047438.

It has also been proposed in European patent application No. EP 80 30 3132, filed Sept. 5, 1980, Dynatech AG (Int. Cl. G 01 N 21/76), to utilize a dispensing device in which liquid feed is effected using a multichannel peristaltic pump.

The above types of dispensing devices are both relatively expensive and not readily adaptable for use in dispensing liquid into a very large number of vessels.

It has further been proposed in U.S. Pat. No. 3,696,971 to Madin (Class 222/183) to arrange for the upper ends of a number of pipettes to open into a large chamber which is subjected to reduced pressure to fill the pipettes with liquid which is then pressurized to dispense the liquid from the pipettes. A similar principle is employed in U.S. Pat. No. 3,982,438 to Byrd (Class 73/425.6) to fill the pipettes and effect dispensing except that, in this case, negative and positive pressure is applied to the pipettes through the intermediary of a flexible diaphragm. The Applicants have found that such devices which rely on the application of negative and positive pressures to effect aspiration and dispensing are expensive and/or do not consistently dispense precisely controlled volumes of liquid.

BRIEF SUMMARY OF THE INVENTION

Accordingly, an object of the present invention is to provide an improved dispensing device which is simple and readily capable of use in dispensing a very large number of precisely controlled volumes of liquid into separate vessels.

According to one aspect of the present invention, there is provided a dispensing device comprising an array of tubes each having an opening at a lower end thereof whereby each tube is open to atmosphere, a support carrying the tubes, a common chamber communicating with the interior of the tubes, and a sealable opening providing communication between said chamber and atmosphere.

With such an arrangement, it is possible to immerse the lower ends of the tubes in a reservoir of liquid to be dispensed with the opening for the chamber unsealed. Liquid will therefore flow into the tubes to a level which is determined by the depth of immersion of the tubes in the liquid, the surface tension effects and wetting effects. The opening is then sealed, for example by placing a finger firmly over the opening. Alternatively, a cover or a valve may be employed for sealing the opening. The device is then moved to a location where dispensing is to take place. Once the finger or cover is removed, the liquid in the tubes will drain out of the latter through the lower ends thereof and into vessels disposed below the tubes. For consistent results, it is of course necessary to ensure that the orientation and depth of immersion of the array of tubes are maintained constant.

As a further way of ensuring consistent dispensing, it is preferred that the tubes be immersed in the liquid to a greater depth than is required and then to raise the tubes to the required depth of immersion before sealing the opening. This ensures that the internal walls of the tubes are wetted in the region of, and immediately above, the desired level of liquid therein, thus reducing inconsistencies which might otherwise occur as a result of variations in surface tension forces. Thus, it is preferred to mount the dispensing device detachably on a support which holds the tubes at the desired position relative to the reservoir but which can be moved downwardly against biasing means so that the tubes can be immersed in the liquid in the reservoir to greater than the desired extent. Release of downward pressure on the support causes the dispensing device to be lifted until the tubes are at the required depth of immersion, following which the opening is sealed and the dispensing device removed and transported to the location at which dispensing is to be conducted.

The tubes may be formed of any desired type of material provided that it is wetted by the liquid to a substantially constant degree and provided that it is not chemically attacked by the liquid to be dispensed. Polypropylene or nylon tubes are preferred from a surface-wetting point of view provided that they are not attacked by the liquid chosen to be dispensed.

In order to minimize the effects of the weight of liquid in the tubes expanding the air in the common chamber and causing liquid to leak from the chamber the volume of the latter is kept to a minimum with the proviso that the cross-section of the air passage defined between the sealable opening and the tubes (such air passage including the common chamber) is not so small as to restrict the flow of air unduly since this would lead to prolonged filling and dispensing times.

To minimize the volume of air in the dispensing device, it is preferred for the upper ends of the tubes to open directly into the common chamber. Likewise, it is preferred for the common chamber to have a height of not more than 2 mm but not less than 0.2 mm.

In the recording of luminescence reactions, it has previously been proposed to utilize very sophisticated and expensive equipment in which either one test is conducted at a time using, for example a photomultiplier tube to measure the luminescence characteristics of a reaction being studied or several photomultipliers are used to monitor several reactions simultaneously. This is not only time consuming but also requires the use of expensive equipment. In order to overcome this problem, it has also been proposed to utilize a photographic technique where luminescence reactions are analysed using containers or vessels to hold the reactants and an instant photographic film to record luminescence. ("INVESTIGATION OF A NOVEL SOLID-PHASE CHEMILUMINESCENT ANALYTICAL SYSTEM, INCORPORATING PHOTOGRAPHIC DETECTION, FOR THE MEASUREMENT OF GLUCOSE" by T. J. N. Carter, T. P. Whitehead and L. J. Kricka-Talanta Vol. 29, pages 529 to 531, 1982) In such a method, tubes are placed in a mask. Then in a darkened room, a shutter covering the film is removed and the assembly of mask and tubes is placed in a film holder so as to cover the sensitive area of the film. Still in the dark, liquid is dispensed into the tubes to initiate the luminescence reaction using a syringe unit. Also, see Industrial Laboratory, Vol. 40, No. 8, February 1975, p. 1118. However, such a technique is difficult to adapt to a large number of reactions because it is effected largely in a darkened room and existing equipment would require the use of a moving shutter to expose only those reaction vessels which can be fed simultaneously with reactant. Thus, not only would a moving shutter be required but also means for indexing the dispensing device, such indexing means being arranged so that indexing of the dispensing device is effected with appropriate light shielding to prevent stray light from reaching the film.

It has been previously proposed in U.S. Pat. No. 3,627,431 to measure the extent of colorimetric reactions photographically by inserting a plurality of tubes into a holder, sliding the holder and tubes into a cabinet containing a light source and shutter in the top of the cabinet and a photographic film in the bottom of the cabinet. Energization of the light source or opening of the shutter exposes the film through the sample tubes. U.S. Pat. No. 3,923,462 discloses apparatus for detecting the concentration of a substance in a fluid, e.g. ozone, in air, by pumping the fluid through a passage in a light tight housing past a disc which luminesces in the presence of the substance to be detected. Photographic film is continuously driven across an optical step wedge disposed on the opposite side of the passage to the luminescent disc so as to provide a continuous record of the degree of luminescence of the disc and thereby a record of the concentration of the substance in the fluid.

European patent application No. EP-8-0019786 discloses a detection device for luminescence reactions which comprises a multi-layer structure including at least one layer having a first reagent system responsive to the presence of an analyte to produce a reaction product, at least one other layer having a second reaction system responsive to the presence of the reaction product to produce luminescence, and a photoresponsive layer responsive to light produced by the second reagent system.

European patent application No. EP-80 30 3132 discloses apparatus for detecting luminescence reactions in which a single row of pipettes and a single row of photodetectors are arranged on opposite sides of a plate carrying an array of reaction wells. The pipettes and photodetectors are mounted on a common support which is driven longitudinally of the plate carrying the array of reaction wells. Such an apparatus is expensive and complicated in that it requires careful synchronization of the various parts of the apparatus to operate correctly.

U.S. Pat. No. 4,027,979 discloses detection apparatus for colorimetric reactions in which light from a light source at the bottom of a housing is individually piped to the undersides of reaction tubes within the housing. The housing can be closed by a cover on which a film holder is provided. Probes extend from the cover in the region of the film holder into the reaction tubes to transport light from the reaction tubes to the photographic film.

European patent application No. EP-8-0071859 (published Feb. 16, 1983) discloses a luminescence detection device in which an opaque reaction vessel housing defines individual reaction vessels which are closed at the top by cannula-piercable portions of the housing. The housing rests on a transparent spacer disposed above a shutter and a photoresponsive imaging layer. The reactions are initiated by liquid injected through the cannula-piercable portions of the housing.

None of the last-described six devices is of a design which lends itself to recording photographically in a simple manner a large number of luminescence reactions which are required to be initiated simultaneously.

It is therefore an object of the present invention to provide an improved recording apparatus for luminescence reactions.

According to another aspect of the present invention, there is provided recording apparatus comprising a holder for a multiplicity of reaction vessels, said holder comprising a plate having an array of holes therein for receiving an array of reaction vessels, a housing for the support, said housing being adapted to be sealed to prevent stray light from entering the housing, means for holding a photographic film adjacent the underside of the plate, and a removable shutter for interposition between the film and the support.

With such an apparatus, it is preferred to use the dispensing device according to the first aspect of the present invention, said dispensing device being arranged so as to close the housing in a light-tight manner with the tubes within the housing. With such an arrangement, the dispensing device is engaged with the housing with the opening remaining sealed, the shutter is removed and the opening in the dispensing device unsealed to allow liquid from the tubes to drain into the individual vessels which have previously been disposed in the support plate. After a predetermined time, the shutter is replaced and the film developed. Obviously, it is preferred for the film to be of the instant type in order to reduce the time required for analysis of the results. Depending upon the period of light emission it may be possible to dispense the liquid before removing the shutter.

Thus, the invention also resides in a combination of the dispensing device according to one aspect of the present invention and the recording apparatus according to the other aspect of the invention.

The light emitted by luminescence reactions is generally of low intensity and so it is usually necessary to employ a very high speed black and white film, for example, a 20,000 ASA film. It is also possible to use high speed color film since chemical reactions can be arranged to produce light of different colors. The apparatus according to the other aspect of the present invention is suitable for use with luminescence reactions having an enhanced light output of the type disclosed in British patent application No. 8206263 entitled "Enhanced Luminescent and Luminometric Immuno Assay".

BRIEF DESCRIPTION OF THE DRAWINGS

The present invention will now be described in greater detail by way of an example, with reference to the accompanying drawings, wherein.

DETAILED DESCRIPTION

Figure 1:
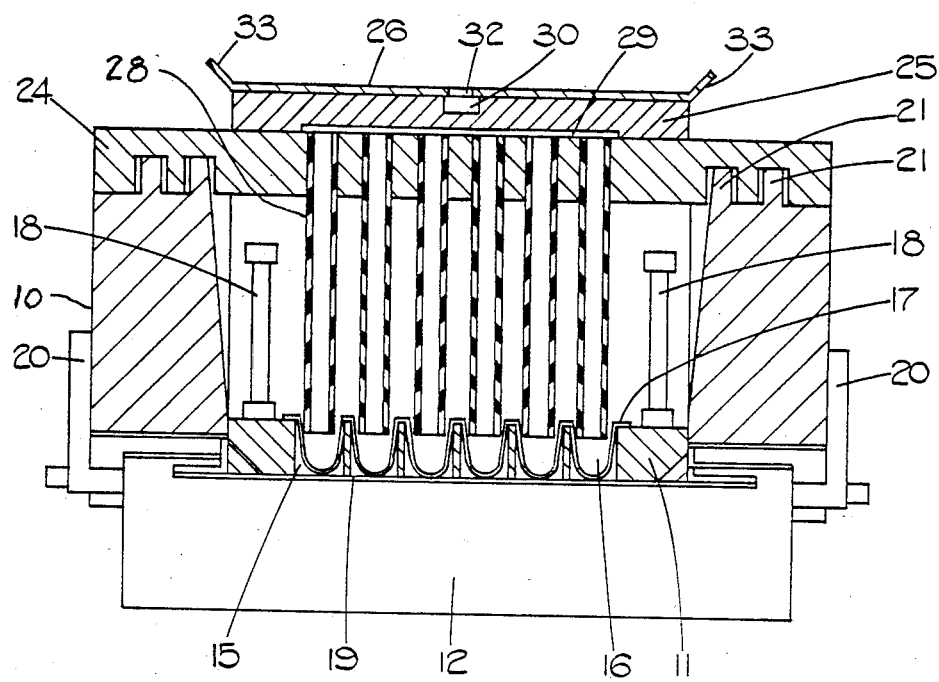
FIG. 1 is a part cross sectional view through recording apparatus according to the present invention incorporating a dispensing device according to the present invention.
Figure 2:
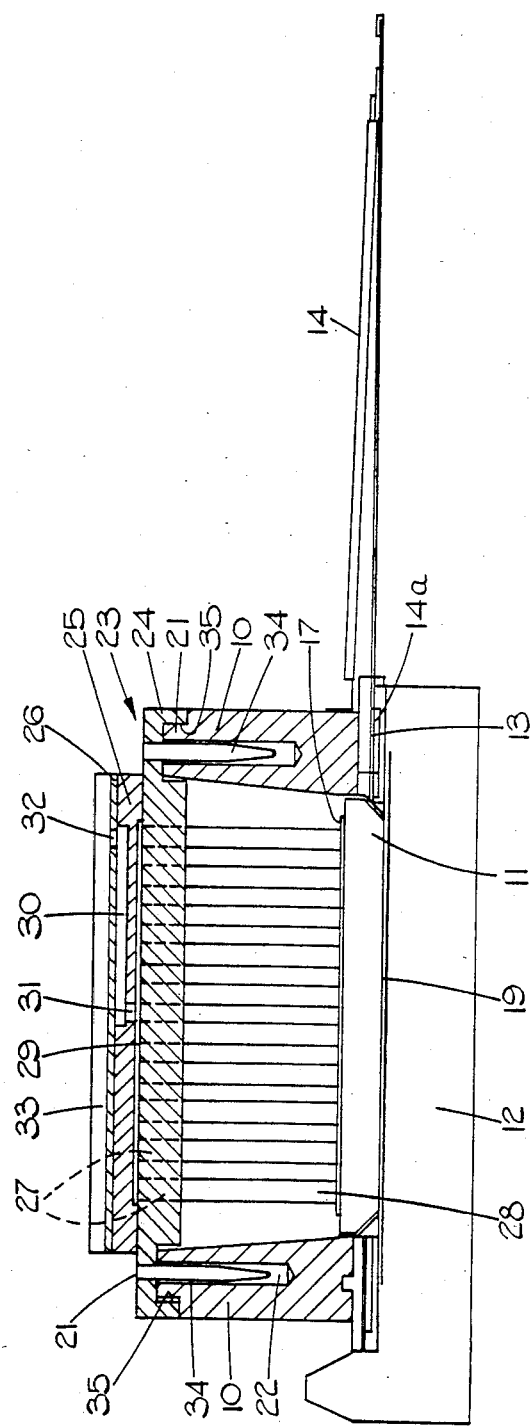
FIG. 2 is a part cross-sectional view of the apparatus of FIG. 1.

Referring now to FIGS. 1 and 2 of the drawings, the recording apparatus comprises basically a housing 10 in the form of a rectangular frame, a support plate 11, and an instant photographic film back 12 secured to the underside of the housing 10 so as to close the otherwise open bottom end thereof. The apparatus further includes a shutter 13 in the form of a thin metal plate which can be slid laterally in and out of the housing 10 between a position in which it lies between the support 11 and the film back 12 and a position in which it completely exposes the film. In this embodiment, the film back 12 is a POLAROID film back containing 20,000 ASA black and white film. A wire cable 14 is connected at one of its ends to the housing 10 and at the other of its ends to an outer end of the shutter 13 in order to limit outward movement of the latter relative to the housing 10 to prevent complete disengagement of the shutter 13 from the housing 10. A felt light trap 14a light proofs the shutter 13. The support 11 has a multiplicity of circular holes 15 therethrough which are spaced apart and arranged in a 10 by 6 array. The holes 15 receive respective small wells 16 in a microtitre plate. The wells 16 are integrally formed with a support sheet 17 out of transparent plastics material. The microtitre plate support sheet 17 rests on the support plate 11 so that the bottoms of the wells 16 lie in the plane of the bottom surface of the support plate 11. The support plate 11 is provided with upstanding studs 18 to enable it to be easily inserted into and removed from the housing 10. When the shutter 13 is in position between the film back 12 and the support plate 11, it supports the latter clear of a photographic film plate in the film back 12. However, when the shutter 13 is slid outwardly of the housing 10 so as to expose the photographic plate completely to the interior of the housing 10, the support plate 11 drops so that it completely engages against the photographic film. In this way, the bottoms of the wells 16 also engage the photographic film. The ends of the support plate 11 are chamfered so that dropping and tilting of the plate 11 and wells 16 occurs smoothly upon movement of the shutter 13. In FIGS. 1 and 2, the photographic film is illustrated at 19.

The film back 12 is secured to the housing 10 by clamps 20. The upper surface of the housing 10 is provided with a pair of upstanding ribs 21 which extend completely around the periphery of the housing 10. Further, the upper surface of the housing 10 is provided with a pair of blind location bores 22 therein (see FIG. 2). The whole of the interior of the housing 10 is given a matt black finish to reduce unwanted internal reflections.

The dispensing device comprises a support 23 formed of a rigid lower plate 24, an intermediate plate 25 and an upper plate 26, all of which plates being rectangular. The lower plate 24 is provided with a 10 by 6 array of holes 27 therethrough in each of which is sealingly secured a NYLON tube 28 which is open at both ends. The upper ends of the tubes 28 are flush with the upper surface of the lower plate 24 whilst the lower ends of the tubes 28 are coplanar and are disposed 38 mm below the lower surface of the plate 24. The intermediate plate 25 is sealingly secured to the upper surface of the plate 24 and has a shallow rectangular recess 29 in its lower surface. The recess 29 extends over the area of the array of holes 27. There is thus defined within the support 23 a shallow chamber (having a depth of 1.0 mm) with which the upper ends of all of the tubes 28 directly communicate. The upper surface of plate 25 is provided with a further recess 30 which is of limited lateral and longitudinal extent. The recess 30 extends from a central hole 31 communicating with recess 29 in the plate 25 to a location adjacent one of the longitudinal ends of the plate 25. The upper plate 26 is sealingly secured to the intermediate plate 25 and has a hole 32 therein which is in register with the end of the recess 30 remote from the hole 31. Longitudinal side edges 33 of the plate 26 project laterally of the plate 25 and are inclined upwardly so as to provide finger grips. The combination of holes 31 and 32 and recess 30 provide, in effect, a labyrinth connection between the outside of the support 23 and the chamber defined partly by the recess 29. This provides a light trap so that external light cannot pass down the tubes 28.

The underside of the lower plate 24 is provided with a spigot 34 at each end thereof, the spigots 34 being engageable in the location bores 22 in the housing 10. The underside of the lower plate 24 is also provided with rectangular peripheral grooves 35 for receiving the ribs 21 of the housing 10 to provide a labyrinth joint between the support 23 and the housing 10. The dimensions of the relevant components are such that, when the dispensing device is in position on the housing 10 (as illustrated in FIGS. 1 and 2), the lower ends of the tubes 28 project a short distance into the wells 16.

Figure 3:
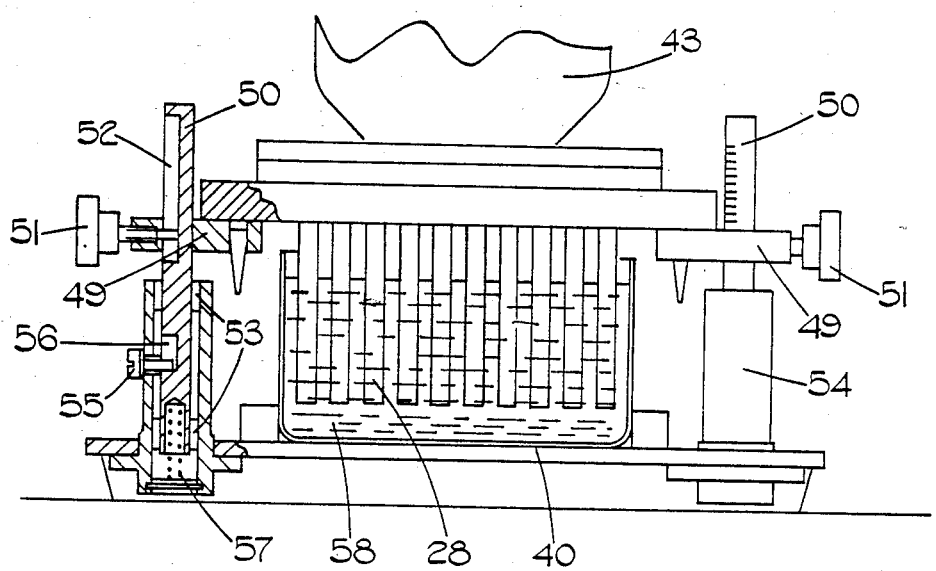
FIG. 3 is a part cross-sectional view illustrating how the dispensing device shown in FIGS. 1 and 2 is filled with liquid to be dispensed.
Figure 4:
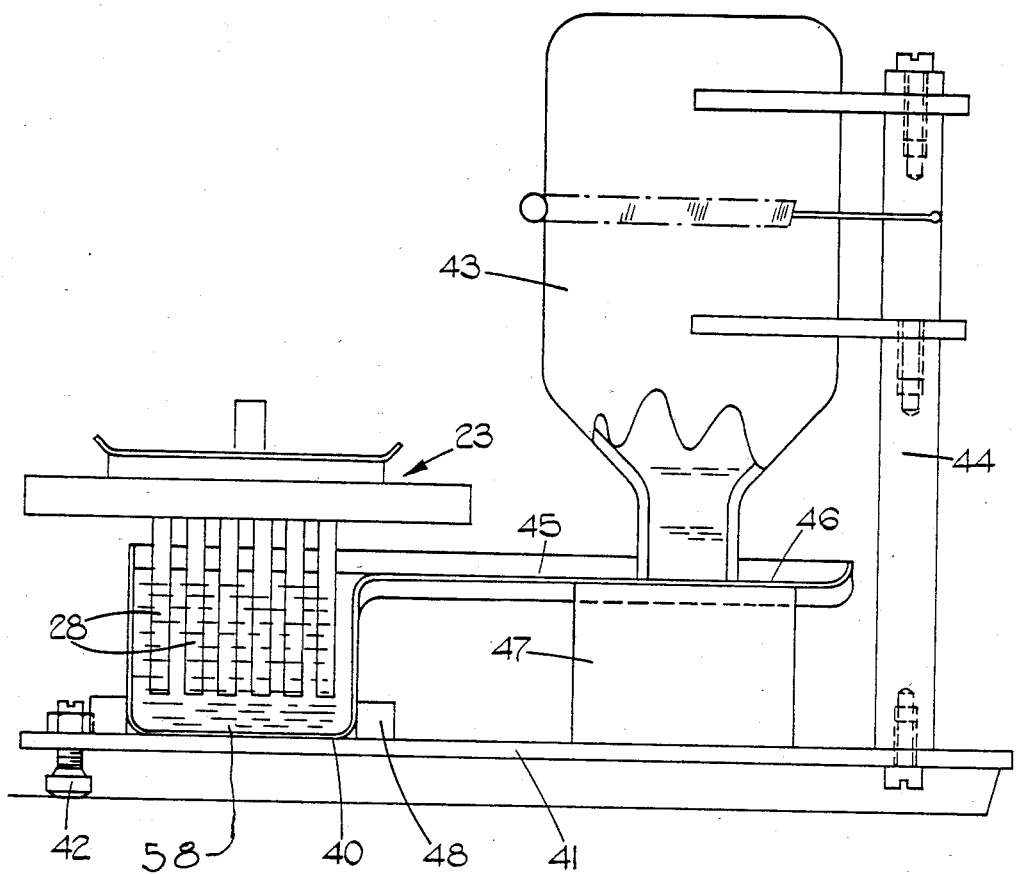
FIG. 4 is a side elevational view of the equipment illustrated in FIG. 3.

Referring now to FIGS. 3 and 4, there is illustrated therein a reservoir 40 for liquid 58 to be dispensed and an associated device for ensuring consistent filling of the dispensing device to the desired level. The reservoir 40 is mounted on a table 41 fitted with adjustable legs 42 to enable the table to be accurately levelled using an XY spirit level (not shown).

The liquid in the reservoir 40 is maintained at a substantially constant level by an arrangement commonly known as a chicken feeder. An inverted bottle 43 supported by a stand 44 is positioned in a channel 45 which communicates with the reservoir 40. The bottle rests on a raised rib 46 in the base of the channel 45 which is supported by a block 47 as shown in FIG. 4. In use, liquid flows out of the bottle 43 until the level of liquid in the reservoir 40 and channel 45 reaches the rim of the bottle 43. Thus, the liquid level in the reservoir 40 remains substantially constant ($\pm \frac{1}{2}$ mm) as the liquid level in the bottle lowers. For economy, when using expensive reagents, the reservoir may be made in the form of a honeycomb of wells to accommodate the tubes 28. In tests where the consistency of the amount of liquid pipetted between multiple samplings is not particularly critical and the liquid is not expensive, a larger reservoir 40 may be used and the "chicken feeder" arrangement omitted.

The reservoir 40 is located on the table 41 by guides 48. The dispensing device is located on support blocks 49 as shown in FIG. 3. These are adjustable vertically on calibrated rods 50 so as to set the depth of immersion of the tubes 2 below the surface of the liquid. The blocks 49 are locked in place by thumb screws 51 acting in slots 52 in the rods 50 to prevent rotation of the blocks 49. The rods 50 are constrained to move vertically in bearings 53 which are held in housings 54. Screws 55 in the housings 54 engage in slots 56 in the rods 50 to limit vertical movement of the rods 50 and prevent axial rotation of the latter. The rods 50 are biased upwards by springs 57. To ensure that each tube holds the same volume, the plane in which the lower ends of the tubes 28 are disposed is kept accurately horizontal during filling and all the tubes are of the same diameter (outer diameter 4.76 mm, inner diameter 3.30 mm). However, in other applications, to obtain a graduation of output volumes, the dispensing device may be tilted and/or the tubes made different lengths or different diameters. This could be used, for example, for producing tones of a pigment or degrees of chemical reaction. The tubes can be made conical so that the lower diameter can enter small vessels whilst having a large internal volume. The tubes may also be sealably fitted to locations in plate 24 and be disposable or be fitted as an array and be disposable. To fill the dispensing device, the latter is placed on the support blocks 49 and pressed down centrally. The stroke is chosen to be greater than the rise of liquid in the tubes 28 due to the surface tension effect and to overcome wetting forces when the tubes 28 are dry. This prewetting of the insides of the tubes 28 ensures that, when the device is released and forced upwards by the springs 57, liquid in all of the tubes 28 rises up by the same amount due to the surface tension effect. The operator seals the hole 32 with a finger and lifts the device clear of the reservoir 40. Alternatively, a tap can be used to open and close the hole 32 and this can be fitted directly to the device or be remote therefrom and be operated manually or automatically. The weight of the columns of liquid in the tubes 28 tends to expand the air within the device causing the liquid to "bulge" at the lower ends of the tubes, this being constrained by the surface tension effect. Lifting the device must be done slowly and carefully so that the surface tension tends to draw any droplets clinging onto the outside of the tubes into the main body of liquid in the reservoir and to prevent liquid flowing or being shaken out from the inside of the tubes. To reduce this latter problem, the volume of air inside the device is kept to a minimum and the outlet diameter of the tubes is kept small. It is difficult to predict the stability of the liquid mathematically since the shock due to human handling is unpredictable. It has been found experimentally that, when dispensing water, and with shock-free level handling, the inside diameter of the tubes 28 should not exceed 6 mm. A minimum internal diameter of 0.5 mm is preferred to ensure that surface tension forces do not dominate over the static head of liquid. The device is then transferred to the recording apparatus and fitted as described above and as shown in FIGS. 1 and 2. The hole 32 is then uncovered causing the liquid to flow out of the tubes 28 into the wells 16 to mix with the liquid therein. The shutter 13 is then withdrawn allowing the microtitre plate and plate 11 to drop onto the photographic film 19. If the luminescence is in the form of a pulse of light, which occurs faster than the time taken to withdraw the shutter, the above two steps are reversed. To obtain good precision, typically 0.9% CV on 200 microlitres, and to prevent premature luminescence, it is important to arrange for the final height of the liquid in the wells to cover the ends of the tubes 28, but to be clear of the initial liquid surface. In this embodiment, the distance from the shutter 13 to the film surface is such that the liquid has to be dispensed first to satisfy the above criteria.

The photographic film records the luminescence and after a short time, typically 30 seconds, the shutter 13 is pushed in. Thus, the dispensing device may then be removed without exposing the film to extraneous light.

The exposed film is then removed from the POLAROID film back 12 causing the developing chemicals to contact the surface and so produce the images. The light areas indicate the presence or absence of an analyte in a sample depending upon the assay used. The degree of lightness and diameter of the image may be used to quantify the analyte. The very fast photographic film used in the apparatus has a high contrast and may not image a continuous gray scale from white to black over the light range produced by the luminescence. Assuming the gray scale is from say 2 to 10 units, for a given exposure time, any luminescence above 10 units will appear white and give no indication of quantity. In order to overcome this, neutral density discs having increasing densities from the center outwards may be sandwiched between the photographic film and the wells 16. Different amounts of analyte will show up as different image diameters.

The above-described apparatus is designed principally as a screening instrument for detecting analyte contained in human blood, for example serum ferritin.

It is imperative that there should be a good means of identifying the samples. The wells 16 and the plate 11 must be correctly orientated and this is achieved by the provision of a locating hole (not shown) in the support sheet 17 of the microtitre plate and a co-operating pin (also not shown) projecting from the plate 11. The lower surface of plate 11 has luminous markings (not shown) corresponding to markings on the microtitre plate. In this way the identification on the microtitre plate is transferred to form permanent images on the film.

The apparatus described above relies upon the operator to remember the sequence of working of the dispensing device and shutter 13. Clearly, if a mistake were made a film could be exposed to extraneous light or a whole batch of patients' samples ruined. It is therefore preferred to couple the dispensing device and the shutter 13 by a simple lever and catch mechanism to permit only the correct sequence to be used.

Figure 5:
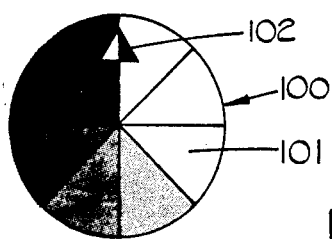
FIG. 5 is a top plan view showing an optical density disc for use in the recording apparatus of FIGS. 1 to 3.

In the above description relating to FIGS. 1 to 3, the optical density discs are described as increasing in density from the center outwardly. In other words, there is a radial variation in optical density. In the embodiment of FIG. 5, each disc 100 is divided into segments 101 each having a different density, the density ranging from zero or a minimum to a maximum density in 360°. The segments may be separated by a dividing line. Thus, there is a circumferential variation in optical density in each disc 100. Instead of being divided into segments 101, the disc 100 may be arranged so that there is a continuous variation in optical density in the circumferential direction.

The variation in light output from the wells in the microtitre plate is usually symmetrical about their longitudinal axes. However, it can vary radially depending upon whether hemispherical or flat-bottomed wells are used. Each segment of the disc 100 as illustrated in FIG. 5 receives a similar illumination from the well with which that disc is associated and the result is measured circumferentially. The images produced on the film by the filter discs 100 are similar to a clock face arrangement, thus making it easy to interpret and describe the results. To assist in viewing the images, a small arrow 102 is provided on each disc 100 to indicate the orientation of the disc on the photographic film.

In some analyses, it may be important to allow only the color produced from a specific luminescent chemical reaction to form an image on the film. In such cases, the discs 100 can be made in the form of varying density coloured filters. These can also be used to distinguish on black-and white film between reactions which produce light of similar intensity but of different colors.

All types of filter described in this application can conveniently be formed by a suitable photographic technique. While the use of filter discs 100 has been described, it will be appreciated that it will generally be more convenient to manufacture a complete matrix containing all of the filters for use in the recording apparatus on a single sheet.

In order to avoid errors, it is important to be able to correlate each result on the film easily in relation to the identity of the specimen from which it is derived. This can be done in a number of ways.

Figure 6:
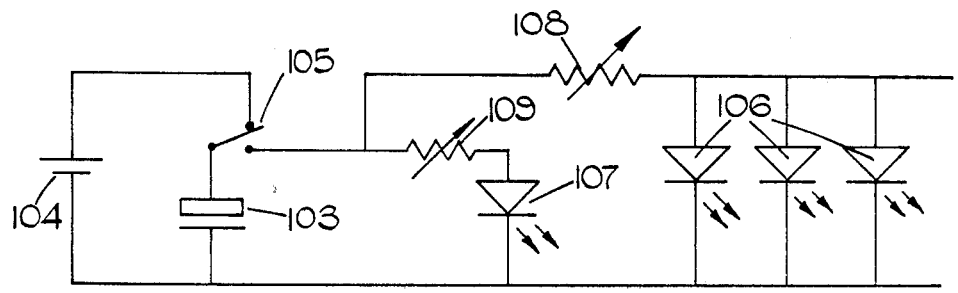
FIG. 6 is a diagram showing a circuit for energizing light emitting diodes used in identification of individual samples.

In one way, the filter matrix is provided with identification markings (eg numbers or letters) thereon corresponding to those on the microtitre plate. It is necessary to illuminate such numbers or letters from behind in order to produce images thereof on the photographic film. This can be effected by a variety of light sources, for example luminescent paint (e.g. made from a liquid scintillant and a radioactive isotope), phosphorescent paint or light emitting diodes. It is considered that the use of discrete light sources in the form of light emitting diodes (LEDs) is most convenient since a short pulse of light can be produced, thus making identification marking of the film independent of the exposure time required to record the chemical reaction. In FIG. 6, there is shown a simple circuit for producing the required pulses of light. A capacitor 103 is charged from battery 104 when 2-position switch 105 is in the position illustrated. When the switch 105 is moved into its other position, capacitor 103 discharges. The setting of resistors 108 and 109 determines the electrical energy supplied to LEDs 106 and 107. The switch 105 may be in the form of a magnetic reed switch which is activated by a magnet built into the shutter of the recording apparatus.

Figure 7:
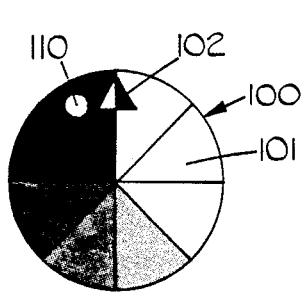
FIG. 7 is a view similar to FIG. 5 showing an alternative form of optical density disc.

Another way of correlating the photographic images with patients' specimens is to use a transparent sheet which is laid over the photographic film when the images on the film are being interpreted. Such a transparent film has letters and/or numbers thereon corresponding to those on the microtitre plate which are in the form of x, y co-ordinates. Alternatively, all results can be marked. To enable the identification characters to be easily read against a black, white or grey background, suitably colored characters or characters in black but having a white surround may be employed. To ensure correct orientation of the transparent film relative to the photographic film, one of the discs 100 at the corner of the sheet can be provided with a suitable marker which is reproduced on the photographic film. Such an arrangement is shown in FIG. 7 where a black circle 110 with a clear center is incorporated into the darkest segment of the disc 100.

As an alternative, the patient identification characters or the indication of the orientation, or both, can be pre-printed on the film.

To ensure that the microtitre plate and the filter matrix plate are in the correct mutual orientation, suitable interlocking means can be provided.

An additional filter disc can be provided in the filter matrix to be used as a reference standard to help identify problems with the apparatus, the film and/or the chemistry of the reaction. This additional filter disc can be illuminated by LED 107.

In the above-described dispensing device precisely measured quantities of a liquid are dispensed simultaneously into wells of the microtitre plate in order to initiate the luminescence reaction.

Figure 9A:
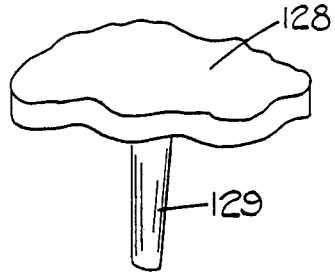
FIGS. 9a to 9d are perspective views showing alternative forms of coated support to that illustrated in FIGS. 8a and 8b.
Figure 9B:
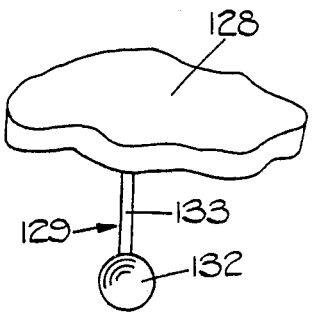
Figure 9C:
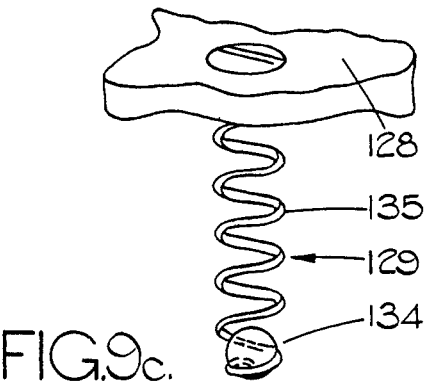
Figure 9D:
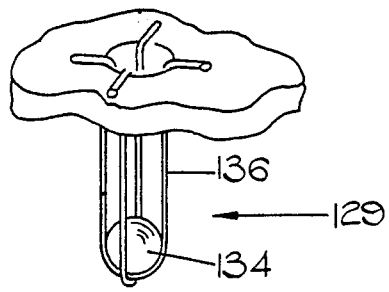
Figure 8A:
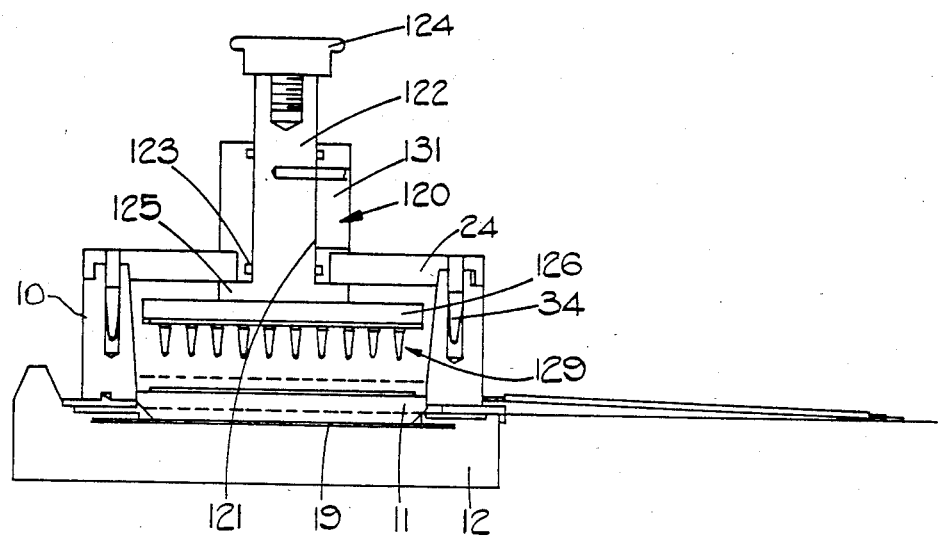
FIGS. 8a and 8b are part cross sectional views similar to FIGS. 2 and 1, respectively of a modified form of recording apparatus.
Figure 8B:
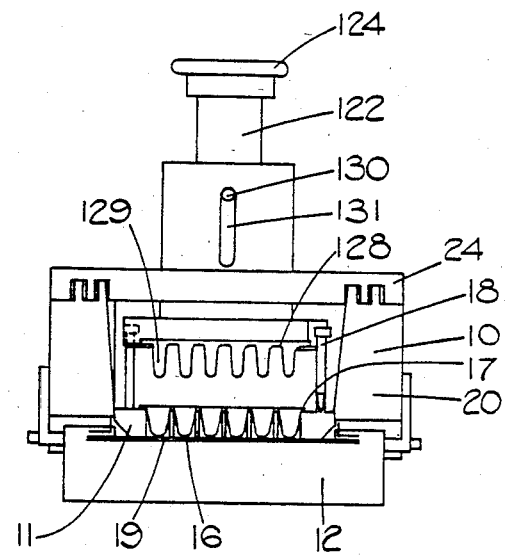

However, the recording apparatus of the present invention is applicable not only to general luminescent reactions occurring in solution but also to immunoassays by coating the inside of the vessels or wells with reagents such as antibodies. Alternatively, coated supports can be dipped into inert reaction vessels containing luminogenic reagent. Such an arrangement is illustrated in FIGS. 8a and 8b where parts of the apparatus which are similar to those of FIGS. 1 to 3 are accorded the same reference numerals. In this embodiment plate 24, which closes the open top of the housing 10 in a light tight manner, is provided with a support block 120 having a vertically extending bore 121 receiving a shaft 122 which is vertically slidable relative to the block 120. Sealing rings 123 in the bore 121 serve to maintain a light-tight construction. The upper end of the shaft 122 has a handle 124 fitted thereto while the lower end thereof terminates in a flange 125 to which a support frame 126 is attached. The support frame 126 carries a coated support array 128 having downwardly extending supports 129. Depression of the handle 124 causes the supports 129, which have previously been coated with initiator, to dip into the liquid in the wells 16 to initiate the luminescence reaction. A peg 130 extending laterally from the shaft 122 engages in an elongated slot 131 in the side of the block 120 to limit the vertical and radial movement of the shaft 122 and thus the movement of the support array 128. As can be seen more clearly in FIG. 9a, each support 129 takes the form of a peg which tapers slightly inwardly in a downward direction. As an alternative, the support array 128 may be provided with supports 129 in the form of balls 132 fixed to the lower ends of rods 133 extending downwards from the main body of the support array 128 (FIG. 9b). Alternatively, the support can take the form of a ball 134 which can be dropped to the bottom of a suitably dimensioned helically wound wire 135 (see FIG. 9c) or wire cage 136 (see FIG. 9d). In alternative embodiments, the supports are physically active, for example they may take the form of ion selective electrodes or fibre optic sensors which are used to measure pH and optical density or light emission, respectively. Thus, it is possible to use luminescence and other analytical techniques simultaneously.

Figure 10:
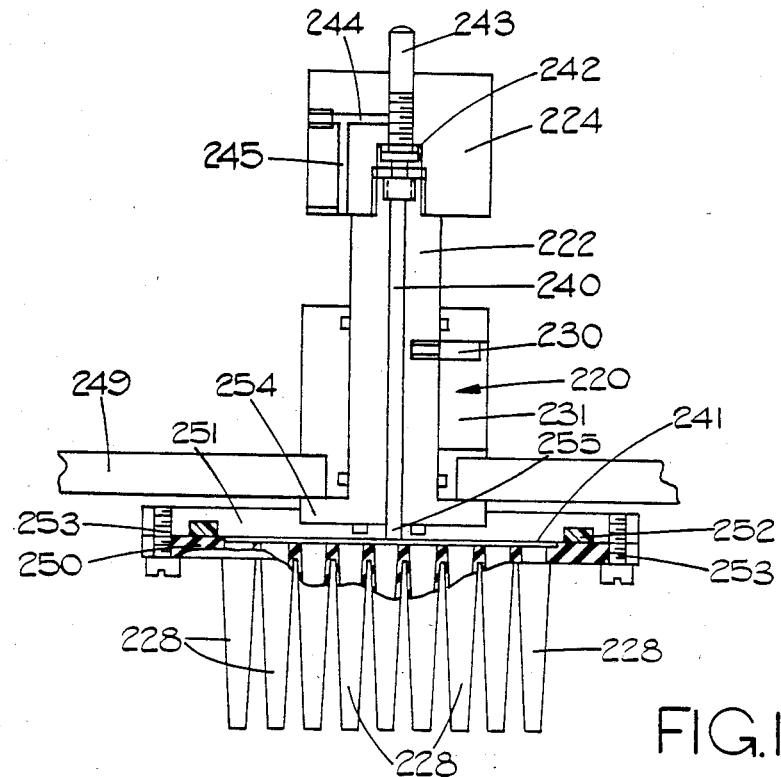
FIG. 10 is a part cross-sectional view of an alternative form of multiple pipette for dispensing liquid into wells in a microtitre plate.

Referring now to FIG. 10, a multiple pipette having downwardly tapering, frusto-conical tubes 228 is, like the flange 125 and supports 129, on the lower end of shaft 222 which is movable vertically in support block 220 carried by a support plate 249 which has an outer periphery (not shown) shaped like that of plate 24 to enable it to be engaged in a light-tight manner with housing 10. In this embodiment, shaft 222 has an axial bore 240 communicating at its lower end with common chamber 241 with which the upper ends of the individual tubes 228 directly communicate. The common chamber 241 is defined, in this embodiment, by a shallow recess in an upper surface of a lower plate 250, the top of the shallow recess being closed by the lower surface of an upper plate 251 secured hermetically to the lower plate 250 using a seal 252 and screws 253. The upper plate 251 is secured to the flange 254 at the lower end of the shaft 222. The depth of the common chamber 241 is 1.0 mm. The tubes 228 are formed of polypropylene and are integrally formed with the lower plate 250 so that the lower plate 250 and the tubes 228 can be formed in a single molding operation. The upper plate 251 has an opening 255 therethrough. The opening 255 provides communication between the bore 240 and the chamber 241. The upper end of the shaft 222 is engaged in screw threaded fashion in handle 224. The handle 224 accommodates a normally closed manually operable valve 242 which, when opened by depression of plunger 243, causes the bore 240 and thus the chamber 241 to communicate with atmosphere via bores 244 and 245 in the handle 224 to permit liquid in the tubes 228 to be discharged into the wells 16. This arrangement enables pretriggering of the reaction to be avoided since it permits the tubes 228 to be moved into the respective wells by downward movement of the shaft 222 only when the reaction is required to be triggered by depression of the plunger. In this respect, it is to be understood that pretriggering of the reaction can occur as the device described with reference to FIGS. 1 to 3 is placed into position since it is possible that liquid which may cling to the sides of the tips of the tubes 228 will enter the wells prematurely. This problem is enhanced because, as the shutter is withdrawn, the microtitre plate is angled. The manually operated valve 243 is more convenient to use than a finger hole. In this embodiment the inside diameter of the tubes 228 at the upper and lower ends thereof is 3.3 mm and 2.0 mm, respectively.

Figure 11:
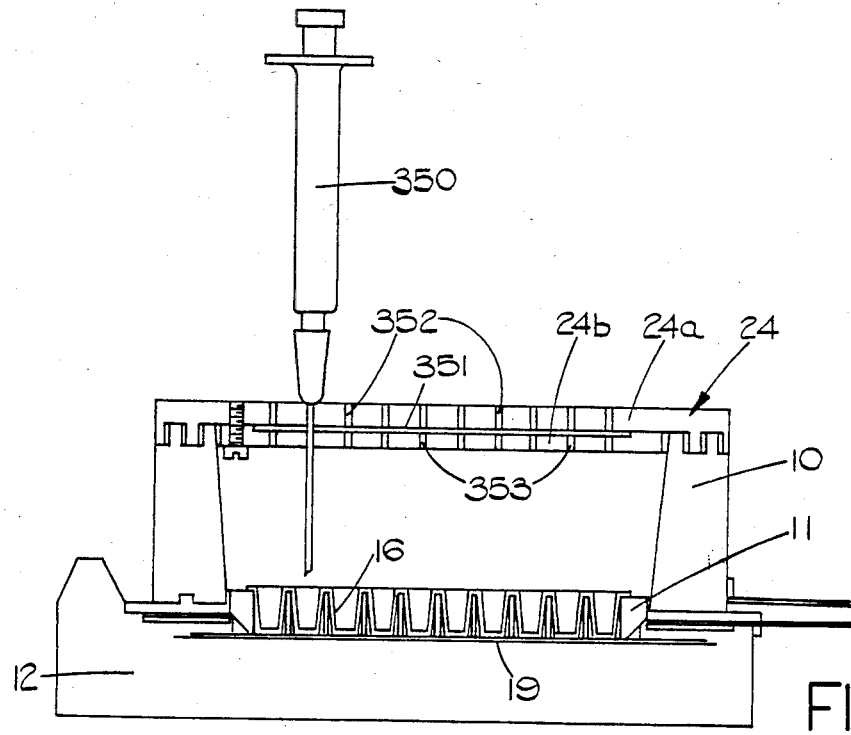
FIG. 11 is a cross sectional view of a modification showing an alternative arrangement for dispensing liquid separately into each well of the microtitre plate.

Referring now to FIG. 11, the liquid dispensing arrangement illustrated therein is designed to allow a conventional syringe 350 to be employed in circumstances where simultaneous supply of liquid to each well 16 is not essential. In this embodiment, the plate 24 is made up of upper and lower parts 24a and 24b and an elastic membrane or septum 351. The septum 351 is sandwiched between the plate parts 24a and 24b which have an array of aligned vertical bores 352 and 353 therethrough.

Each pair of aligned bores 352 and 353 is disposed vertically above a respective one of the wells 16. The needle of the syringe 350 can penetrate the septum 351 without allowing light into the apparatus.

The microtitre plate can itself act as a light guide so that light from a highly reactive specimen can contaminate the results obtained from neighboring specimens. To overcome this, the microtitre plate may be formed of a material which, although light transmitting, absorbs a proportion of the light so that light conduction between cells is greatly attenuated without greatly affecting light within a cell. For this purpose, the material may be colored to absorb light of a specific wavelength or possess wide absorption characteristics typical of a neutral density filter.

A similar problem may arise with light conduction through the tips of the tubes causing contamination of the results. This can be overcome by employing tube tips formed of translucent material as opposed to completely transparent material. An opaque material is not desirable since this would obscure observation of the liquid in the pipette tips.

We claim:
1. A dispensing device comprising:
 a tube support member;
 a plurality of vertically extending tubes supported at the upper ends thereof in said support member in spaced array, said tubes being open at both ends;
 a common chamber in said support member communicating with the open upper ends of said tubes; and
 a sealable opening through said support member communicating said chamber with the atmosphere so that said tubes are simultaneously filled with fluid a predetermined amount by immersing the lower ends thereof to a predetermined depth in a body of fluid with said sealable opening unsealed and thereafter sealing said opening to retain said fluid in said tubes when said tubes are removed from the body of fluid and unsealing said opening to dispense the fluid retained in said tubes therefrom.

2. A device as claim in claim 1 wherein the maximum internal diameter of each tube 6 mm.

3. A device as claimed in claim 2 wherein the minimum internal diameter of each tube is 0.5 mm.

4. A device as claimed in claim 1, wherein said upper ends of the tubes extend through said support member so that the upper ends thereof are flush with and communicate directly with the common chamber (29, 241).

5. A device as claimed in claim 1 and further comprising:
 a normally closed valve operatively mounted in said sealable opening to close said opening; and
 means to selectively open said valve.

6. A device as claimed in claim 1 wherein:
 said support member comprises two planar members held together in sealed parallel relationship at an interface therebetween; and
 said common chamber comprises a shallow recess between said two planar members at said interface.

7. A device as claimed in claim 6 wherein:

said tubes and one of said planar members are comprised of an integral one-piece construction.

8. A device as claimed in claim 6 wherein:
said planar members are comprised of lower and intermediate plates;
a plurality of holes are provided through said lower plate; and
said tubes are mounted in said holes.

9. A device as claimed in claim 8 wherein:
said planar members are further comprised of an upper plate sealingly mounted on said intermediate plate; and
said sealable opening comprises a light-tight passage in said intermediate plate and an outer opening through said upper plate communicating with said passage.

10. A device as claimed in claim 1 and further comprising:
a base member;
a support for said tube support member mounted on said base member;
a container mounted on said base member for containing the body of fluid;
said tube support member being supported on said support with the lower ends of said tubes immersed in the body of fluid said predetermined amount; and
means to resiliently support said support on said base member for limited downward movement of said support so that said tubes can be immersed in said body of fluid a limited amount greater than said predetermined amount.

11. A device as claimed in claim 10 wherein said support comprises:
a plurality of tubular support housings mounted on said base member and extending upwardly therefrom;
a support rod slidingly mounted in each housing; and
wherein said resilient support means comprises a spring means operatively disposed between each housing and respective rod therein.

12. A device as claimed in claim 11, wherein means are provided for maintaining a constant liquid level in the reservoir.

13. A device as claimed in claim 1 and further comprising:
a light-tight hollow housing having a bottom plate, said support member being the upper cover of the housing;
a plurality of reaction vessels supported on said lower plate in spaced array conforming with the array of spaced tubes;
means for holding a photographic film adjacent the underside of said bottom plate; and
a removable shutter interpositioned between said bottom plate and the photographic film.

14. A device as claimed in claim 13 and further comprising:
means for mounting said tube on said tube support member for movement relative thereto towards and away from said bottom plate.

15. A device as claimed in claim 13 wherein said device further comprises a recording apparatus:
a plurality of openings in spaced array are provided in said bottom plate for receiving said reaction vessels; and
sealing means are provided to prevent entry of stray light into the housing, said tubes being within said housing.

16. A device and apparatus as claimed in claim 15 wherein:
said sealing means comprises at least one set of cooperating mutually interengageable ribs and grooves on said support member and housing extending around the area of contact between said support member and housing.

17. Device and recording apparatus as claimed in claim 15, wherein the shutter is arranged, when in a closed position, to hold the plate clear of the film and, when in an opened position, to allow the plate to drop so that its lower surface engages against the photographic film.

18. Device and recording apparatus as claimed in claim 15, wherein a member is provided between at least one of the vessels and the film, said member having portions of different optical transmission characteristics through which, in use, light from each vessel passes to the film.

19. Device and recording apparatus as claimed in claim 18, wherein said member is in the form of a disc.

20. Device and recording apparatus as claimed in claim 19, wherein a plurality of discs are provided as parts of a sheet.

21. Device and recording apparatus as claimed in claim 19 wherein the discs have transmission characteristics which vary circumferentially of the discs.

22. Device and recording apparatus as claimed in claim 22, wherein the portions of different transmission characteristics are of segmental form.

23. Device and recording apparatus as claimed in claim 18, wherein the member having portions of different optical transmission characteristics is a graduated neutral density filter.

24. Device and recording apparatus as claimed in claim 15, further including means for correlating the individual images on said photographic film with the individual reactions which are conducted, in use in the vessels.

25. Device and recording apparatus as claimed in claim 24, wherein the correlating means comprises identification markings adjacent to some or all of the holes in said bottom plate, and an illumination means for transferring the identification markings onto the photographic film.

26. Device and recording apparatus as claimed in claim 25, wherein the illumination means includes a plurality of discrete light sources and means for controlling illumination of the discrete light sources.

27. Device and recording apparatus as claimed in claim 26, wherein the discrete light sources are light emitting diodes.

28. Device and recording apparatus as claimed in claim 29, including at least one or more fixed intensity light sources for producing at least one reference images on the photographic film.

29. Device and recording apparatus as claimed in claim 24, wherein the correlating means comprises a separate overlay sheet which is laid over the photographic film when interpreting the images thereon.

30. Device and recording apparatus as claimed in claim 16 wherein the support member is arranged so as to permit the tubes to be moved towards and away from said bottom plate having the array of openings therein.

31. Device and recording apparatus as claimed in claim 15, wherein the support member caries an array of supports for a reagent.

32. Device and recording apparatus as claimed in claim 31, wherein said support member is arranged to carry the array of supports for movement relative thereto towards and away from said bottom plate.

* * * * *